US010826535B2

(12) United States Patent
Abdellatif et al.

(10) Patent No.: US 10,826,535 B2
(45) Date of Patent: Nov. 3, 2020

(54) DEVICE AND METHOD FOR COMPRESSING A DATA STREAM

(71) Applicant: Qatar Foundation for Education, Science and Community Development, Doha (QA)

(72) Inventors: Alaa Awad Abdellatif, Doha (QA);
Amr Mohamed, Doha (QA);
Carla-Fabiana Chiasserini, Doha (QA)

(73) Assignee: Qatar Foundation for Education Science and Community Development, Doha (QA)

( * ) Notice: Subject to any disclaimer, the term of this patent is extended or adjusted under 35 U.S.C. 154(b) by 0 days.

(21) Appl. No.: 16/375,286

(22) Filed: Apr. 4, 2019

(65) Prior Publication Data

US 2019/0319642 A1 Oct. 17, 2019

(30) Foreign Application Priority Data

Apr. 5, 2018 (GB) .................................. 1805628.3

(51) Int. Cl.
*H03M 7/30* (2006.01)
*H03M 13/15* (2006.01)
*A61B 5/0476* (2006.01)

(52) U.S. Cl.
CPC ......... *H03M 13/156* (2013.01); *A61B 5/0476* (2013.01); *H03M 7/30* (2013.01)

(58) Field of Classification Search
CPC ...... H03M 13/156; H03M 7/30; A61B 5/0476
USPC ........................................................ 375/260
See application file for complete search history.

(56) References Cited

U.S. PATENT DOCUMENTS

| 5,905,758 | A | 5/1999 | Schweiter et al. |
| 6,668,097 | B1 * | 12/2003 | Hu .......................... G06T 5/001 |
| | | | 375/E7.19 |
| 6,757,913 | B2 | 6/2004 | Knox |
| 9,473,197 | B2 | 10/2016 | Longhurst |

(Continued)

FOREIGN PATENT DOCUMENTS

| EP | 2 951 930 A1 | 12/2015 |
| GB | 2 460 012 | 11/2009 |

*Primary Examiner* — Kevin M Burd
(74) *Attorney, Agent, or Firm* — Foley & Lardner LLP

(57) ABSTRACT

We provide a method of compressing a data stream for transmission, including: generating a data sequence representing a received data stream, generating a plurality of data substreams, each comprising a portion of the data sequence, identifying a formal concept defining a dependency between a first one of the data substreams and one or more further ones of the data substreams that are dependent on the first data substream, removing those dependent data substreams from the plurality of data substreams, and transmitting the remaining data substreams, and a method of reconstructing a data stream at a receiver, including: receiving a received data sequence representing a received data stream, identifying that a substream has been removed from the data stream prior to transmission, identifying a formal concept definition for regenerating the removed substream based on an identified substream of the received data sequence, regenerating a data substream using the formal concept definition and the identified substream of the received data sequence, and adding the regenerated data substream to the received data sequence.

16 Claims, 11 Drawing Sheets

(56) References Cited

U.S. PATENT DOCUMENTS

Figure 1:
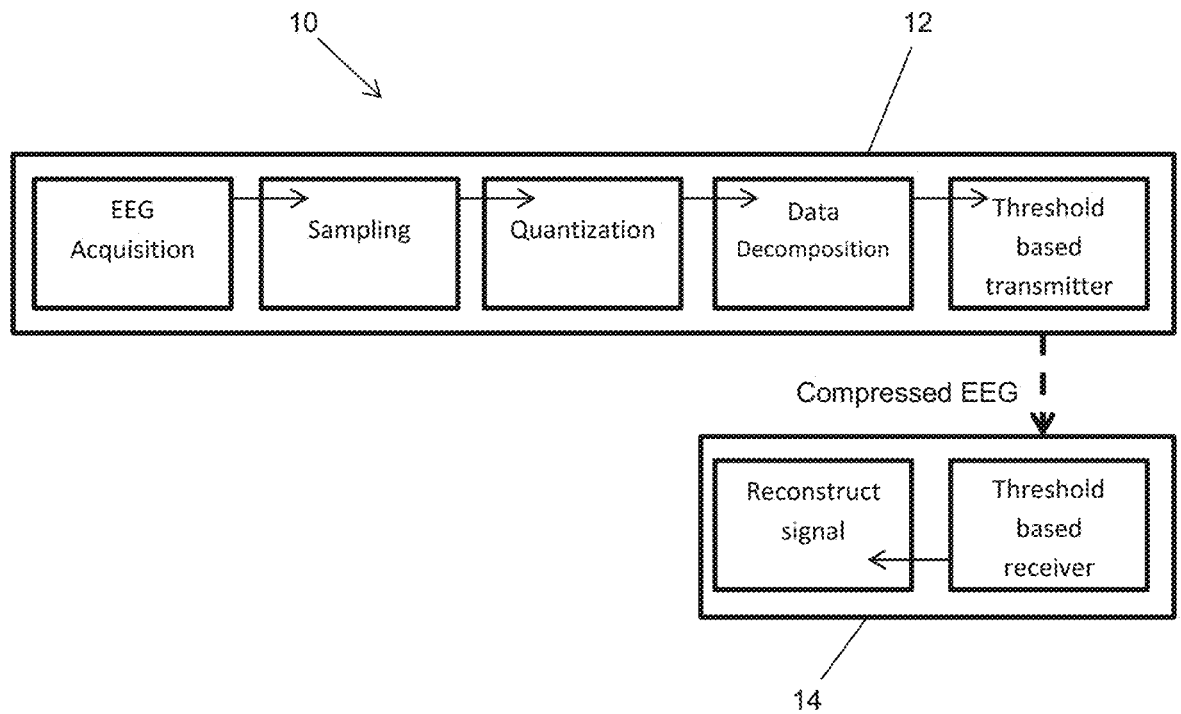

| | | | |
|---|---|---|---|
| 2010/0034187 A1* | 2/2010 | Kumar | H04L 49/90 370/345 |
| 2012/0078852 A1* | 3/2012 | Haselton | G06F 11/1451 707/654 |
| 2015/0199010 A1* | 7/2015 | Coleman | A61B 5/0006 345/156 |
| 2018/0026649 A1* | 1/2018 | Harik | H03M 7/3082 707/693 |
| 2018/0138921 A1* | 5/2018 | Arelakis | H03M 7/6088 |
| 2019/0166576 A1* | 5/2019 | Kim | H04W 76/15 |

* cited by examiner

|    | S1 | | | | S2 | | | | S3 | | | | S4 | | | | ..... | S17 | | | | S18 | | | | S19 | | | | S20 | | | |
|----|---|---|---|---|---|---|---|---|---|---|---|---|---|---|---|---|---|---|---|---|---|---|---|---|---|---|---|---|---|---|---|---|---|
|    | 0 | 1 | 2 | 3 | 0 | 1 | 2 | 3 | 0 | 1 | 2 | 3 | 0 | 1 | 2 | 3 | | 0 | 1 | 2 | 3 | 0 | 1 | 2 | 3 | 0 | 1 | 2 | 3 | 0 | 1 | 2 | 3 |
| O1 | 0 | 1 | 0 | 0 | 0 | 0 | 1 | 0 | 0 | 0 | 1 | 0 | 0 | 1 | 0 | 0 | ..... | 0 | 1 | 0 | 0 | 0 | 0 | 1 | 0 | 0 | 1 | 0 | 0 | 0 | 1 | 0 | 0 |
| O2 | 0 | 0 | 0 | 1 | 1 | 0 | 0 | 0 | 1 | 0 | 0 | 0 | 0 | 0 | 0 | 1 | ..... | 0 | 0 | 0 | 1 | 1 | 0 | 0 | 0 | 0 | 0 | 0 | 1 | 0 | 0 | 0 | 1 |
| O3 | 0 | 0 | 0 | 1 | 1 | 0 | 0 | 0 | 1 | 0 | 0 | 0 | 0 | 0 | 0 | 1 | ..... | 0 | 0 | 0 | 1 | 1 | 0 | 0 | 0 | 0 | 0 | 0 | 1 | 0 | 1 | 0 | 0 |
| O4 | 0 | 1 | 0 | 0 | 0 | 1 | 0 | 0 | 0 | 1 | 0 | 0 | 0 | 0 | 0 | 1 | ..... | 0 | 0 | 0 | 1 | 1 | 0 | 0 | 0 | 0 | 1 | 0 | 0 | 1 | 0 | 0 | 0 |
| O5 | 0 | 1 | 0 | 0 | 1 | 0 | 0 | 0 | 0 | 1 | 0 | 0 | 0 | 1 | 0 | 0 | ..... | 0 | 1 | 0 | 0 | 1 | 0 | 0 | 0 | 0 | 1 | 0 | 0 | 0 | 0 | 0 | 1 |
| O6 | 0 | 0 | 1 | 0 | 0 | 0 | 1 | 0 | 1 | 0 | 0 | 0 | 0 | 0 | 1 | 0 | ..... | 0 | 0 | 1 | 0 | 1 | 0 | 0 | 0 | 0 | 0 | 1 | 0 | 0 | 1 | 0 | 0 |

DEVICE AND METHOD FOR COMPRESSING A DATA STREAM

CROSS-REFERENCE TO RELATED PATENT APPLICATION

This application claims priority from United Kingdom Application No. 1805628.3, filed Apr. 5, 2018, which is incorporated herein by reference in its entirety.

DESCRIPTION OF INVENTION

The present invention relates to an improved method of and a device for transmitting a data stream. In particular, the invention relates to a method of compressing a data stream before transmission, and of reconstructing a received signal to reform the data stream, and to transmitters and receivers configured to carry out the methods.

The emergence of Internet of Things (IoT) applications and rapid advances in wireless communication technologies have motivated a paradigm shift in the development of viable applications such as mobile-Health. These applications boost the opportunity for ubiquitous real-time monitoring using various data types such as Electroencephalography (EEG), Electrocardiography (ECG), among others. However, many remote monitoring applications require continuous or near-continuous sensing for different signals and vital signs, which result in generating large volumes of real time data which must be processed, recorded, and transmitted. Thus, designing efficient transceivers is crucial to reduce transmission delay and energy usage, through leveraging data reduction techniques.

The rapid advances in Edge Computing, communication technologies, Internet of Medical Things (IoMT), and Big Data have facilitated the development of Mobilehealth (m-health) systems that support gathering, delivery, and retrieval of healthcare information. M-health systems leveraging the wide range of mobile technologies (e.g. smartphones, tablets, and portable health devices) enable providing efficient continuous-remote healthcare services, or known as ubiquitous healthcare. M-Health applications are expected to inspire fundamental transformations for the healthcare industry toward Healthcare Industry 4.0 (Health 4.0), especially in pre-hospital emergency care situations and for geographically remote areas. The main goal of Health 4.0 is to enable the automation and personalization of all medical processes through leveraging medical cyber-physical systems, IoMT, and Edge/Cloud computing. Health 4.0 allows, on one hand, patients to monitor their health without the necessity of visiting the hospital or clinic. On the other hand, the hospitals/caregivers can provide patients with medical services through computerized medical information systems. Despite these major trends, new challenges have emerged due to the massive real-time data collected as part of health monitoring systems. Healthcare applications require processing and wireless delivery of intensive data to ensure the quality of healthcare services. This obviously sets a significant load on the system design in terms of processing capabilities, storage space, and power consumption. In addition to that, m-health systems typically consist of several battery-operated devices that should run for a long time without replacement, hence enabling transmission of large volumes of data in such systems continuously increases the energy consumption and complexity of radio frequency (RF) transceivers.

To address this shortcoming and meet diverse requirements of next-generation wireless networks, and IoMT applications, different modules of physical layer need to be optimized so that they can be flexibly configured based on the technical requirements of each application. In this context, we provide an efficient EEG-based transceiver design that maintains application Quality-of-Service (QoS) requirements (i.e., signal distortion) taking into consideration the characteristics of the acquired data, while saving a significant amount of transmitted data. We argue here that devoting transceiver design to be specific for a certain type of data (e.g. EEG) is perfectly in consistence with IoMT devices that mostly acquire one type of data efficiently (e.g. using Emotiv headset, or QardioCore wireless Electrocardiography (ECG) monitor). Hence, leveraging the characteristics of such data at the physical layer will have positive effects on the costs as well as on the energy consumption of the RF transceiver.

The EEG signal is the main source of information on brain electrical activities which plays an important role in the diagnosis of several brain disorders, and has a primary role in Brain Computer Interface (BCI) applications.

The goal of most new transmission techniques and compression techniques, until now, has been to find techniques that can be used widely, across all technologies, and that are suitable to send and receive data of all types. Current compression techniques inherently involve some degree of data loss or distortion in order to achieve lower data usage, and such losses are either accommodated by use of complex reconstruction techniques that may analyse and recompose data streams at high computational cost (resulting in losses in efficiency and speed) or else the data losses are accepted as an inherent performance constraint. Most existing compression techniques are applied at the higher layers of abstraction, while ignoring lower layers' features (e.g., characteristics of wireless channels, signal-to-interference-plus-noise ratio (SINK), and bit/symbol error rate). Also, consequent computational complexity can mean that implementing such schemes on battery-operated devices is inefficient and impractical.

The present invention seeks to ameliorate or overcome one or more problems associated with the prior art.

The present invention relates to an efficient data-specific method of compression resulting in a transceiver design that leverages the inherent characteristics of the generated data at the physical layer to reduce transmitted data size without significant overheads. The aim of the technique is to reduce the amount of data that needs to be transmitted in order to efficiently communicate (and optionally store) information, while maintaining the required application Quality-of-Service (QoS) requirements.

These techniques can be used to achieve excellent performance in terms of data reduction gain, low signal distortion and low complexity. Devices configured to use these techniques may achieve about 50% compression ratio at 0% distortion and sample error rate.

A first contribution of the present invention lies in the design of an efficient EEG-based transceiver that leverages the characteristics of the EEG signals at the physical layer in order to provide an efficient transmission, while maintaining application level QoS. Leveraging the exiting orthogonal frequency division multiplexing (OFDM) transceiver's components, the proposed method performs the data compression task as part of the physical layer, hence leading to an efficient compression scheme with no significant overhead.

Furthermore, the present invention provides decomposition of generated data into multiple streams to further increase compression ratio through applying different compression thresholds for each stream, and discovering the dependency between different streams.

The proposed design is evaluated through simulations discussing the tradeoff between transmitted data length and signal distortion. Results of testing demonstrate the gain provided by this method, and its ability to obtain high lossless and lossy compression ratios.

We provide an efficient transceiver design that relies on OFDM technology while obtaining an adaptive compression method in order to control the size of the transmitted data. OFDM is a well-designed technology for high-rate wireless communication. However, the performance of such systems is generally limited by the available transmission energy. Thus, we can save in energy consumption through compressing the data before transmission, while retrieving the original data at the receiver side with zero or low distortion depending on the applied compression ratio and application requirements.

According to a first aspect of the invention we provide a method of compressing a data stream for transmission, including:

generating a data sequence representing a received data stream, generating a plurality of data substreams, each comprising a portion of the data sequence, identifying a formal concept defining a dependency between a first one of the data substreams and one or more further ones of the data substreams that are dependent on the first data substream, removing those dependent data substreams from the plurality of data substreams, transmitting the remaining data substreams.

The step of identifying a formal concept may include identifying a plurality of formal concepts, each defining a dependency between a first one of the data substreams and one or more of the further ones of the data substreams that are dependent on the first data substream.

The method may include the step of transmitting data representative of the formal concept for use in reconstructing the removed data substreams at the receiver.

The data stream may be an EEG data stream, comprising data from an electroencephalogram.

The method may include transforming the data stream using a Fast Fourier Transform or its inverse to convert the data stream from the time domain to the frequency domain.

The method may include applying a threshold $\delta$ to the data stream such that values less than $\delta$ are rounded to zero.

The method may include a step of further compressing the data stream by removing occurrences of sequential consecutive zero values in the data stream and replacing those removed sequences of zeros with data representing the length of the sequence of consecutive zeros removed.

According to a second aspect of the invention we provide a device comprising a transmitter, the device being configured to compress a data stream for transmission according to the method of the first aspect.

According to a third aspect of the invention we provide a method of reconstructing a data stream at a receiver, including:

receiving a received data sequence representing a received data stream, identifying that a substream has been removed from the data stream prior to transmission, identifying a formal concept definition for regenerating the removed substream based on an identified substream of the received data sequence, regenerating a data substream using the formal concept definition and the identified substream of the received data sequence, and adding the regenerated data substream to the received data sequence.

The step of identifying a formal concept may include identifying a plurality of formal concepts, each defining a dependency between a first one of the data substreams and one or more of the further ones of the data substreams that are dependent on the first data substream.

Identifying the formal concept may include receiving data representative of the formal concept.

Identifying the formal concept may include accessing data stored at the receiver representative of the formal concept.

The method may further include transforming the data stream using a Fast Fourier Transform or its inverse to convert the data stream from the frequency domain to the time domain.

The method may further include identifying, in the received data sequence, data representing the length of a sequence of zeros removed from the data stream prior to transmission, and inserting a sequence of zeros of the identified length in the received data sequence.

According to a fourth aspect of the invention we provide a device comprising a receiver, the device being configured to reconstruct a data stream according to the method of the third aspect.

According to a fifth aspect of the invention we provide a transceiver comprising a combination of a transmitter being configured to compress a data stream for transmission according to the method of the first aspect and a receiver configured to reconstruct a data stream according to the method of the second aspect.

In summary of the concepts involved in the present methods and devices, we provide a transceiver design based on symbol-streams compression: the generated symbols are grouped into streams, and only streams that are independent of each other are compressed and transmitted. Additionally, streams are compressed separately, thus the compression thresholds can be tailored to each stream so that the compression ratio is increased while yielding low distortion. In the context of EEG signals we have demonstrated how the Fourier coefficients representing such signals can be effectively compressed while accounting for the wireless channel characteristics and the application requirements in terms of signal distortion.

Notably, the transceiver is compatible with the current 4G standard and the evolving requirements of next-generation networks since it relies on the OFDM technology with two simple added modules. The simulation results discussed below highlight the benefits of the methods in terms of overall compression ratio and signal distortion, with the remarkable result of 50% compression ratio at zero distortion and sample error rate.

Figure 2:
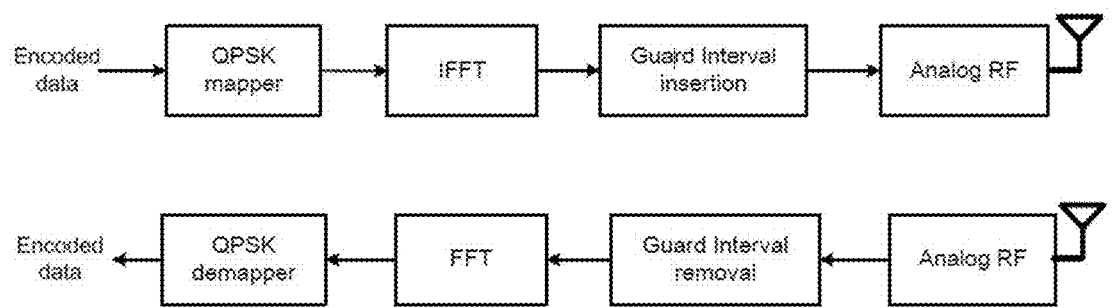
Figures 3, 4:
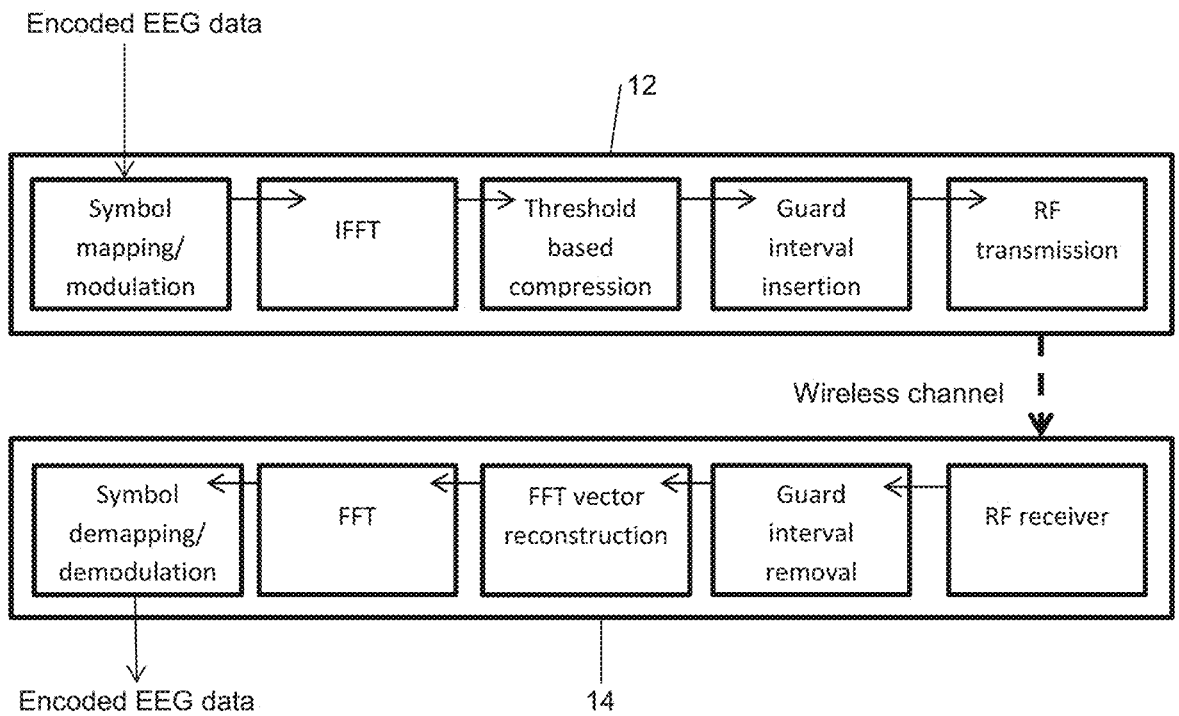
Figure 5:
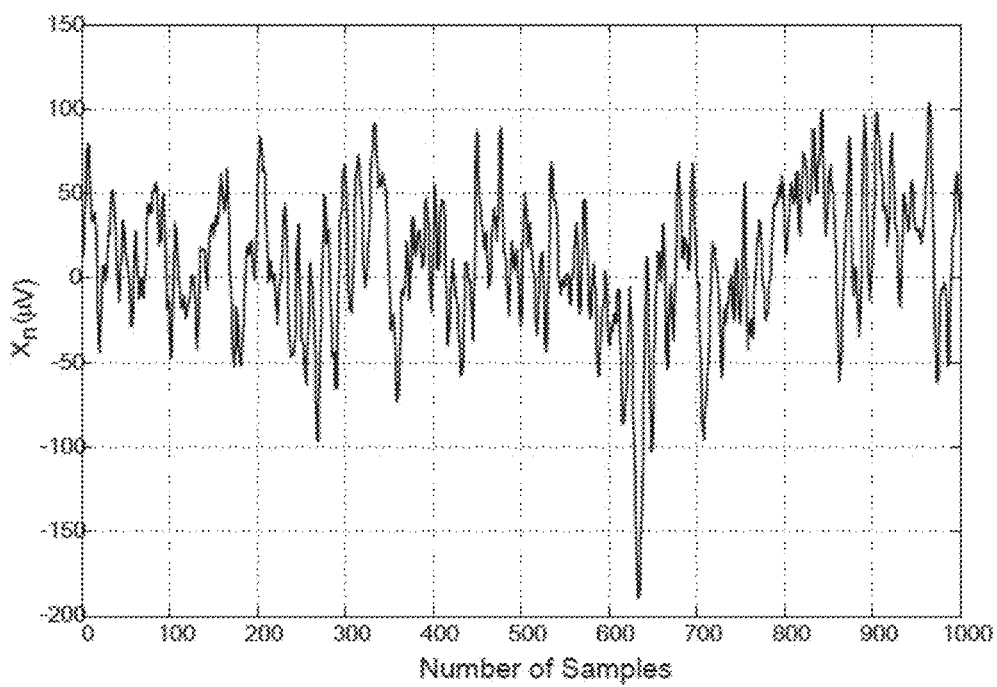
Figure 6:
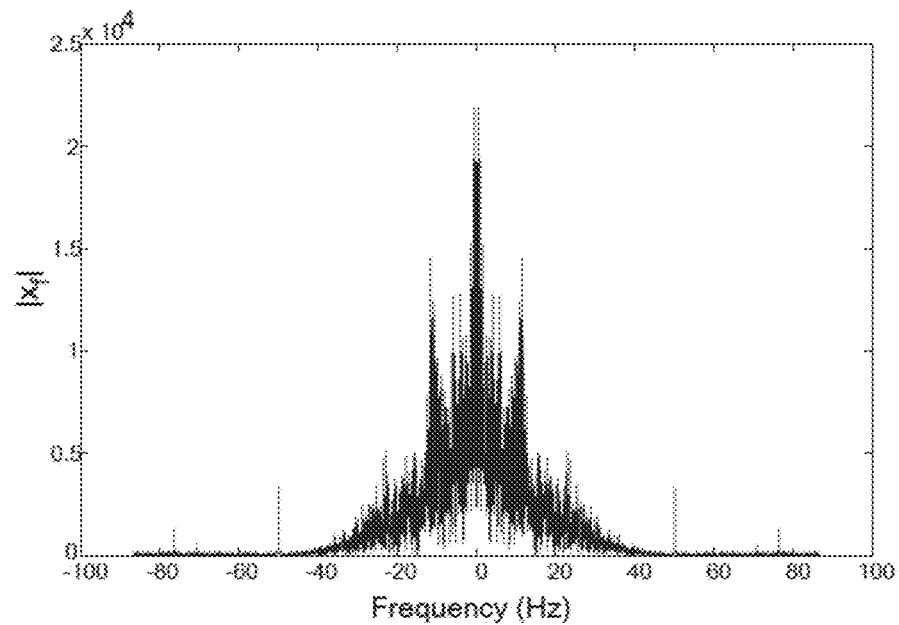
Figure 7:
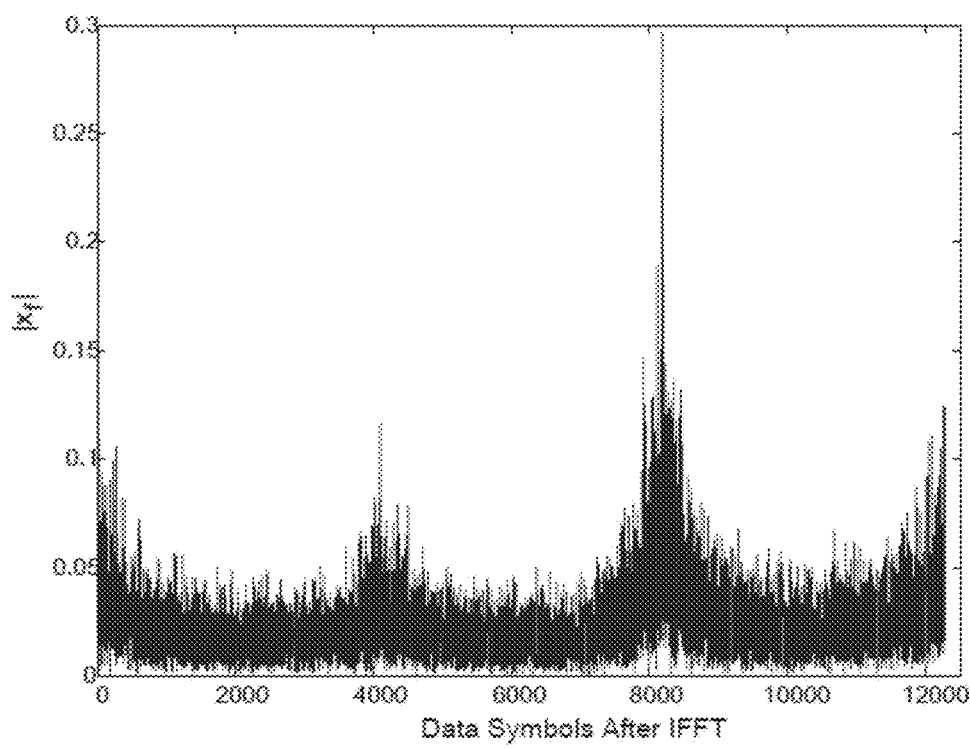
Figure 8:
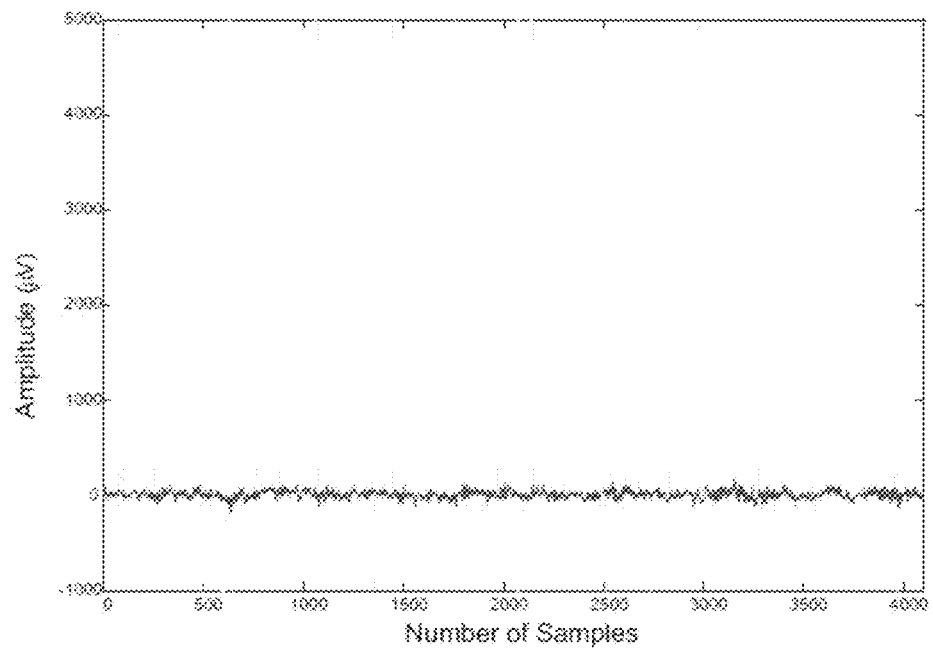
Figure 9:
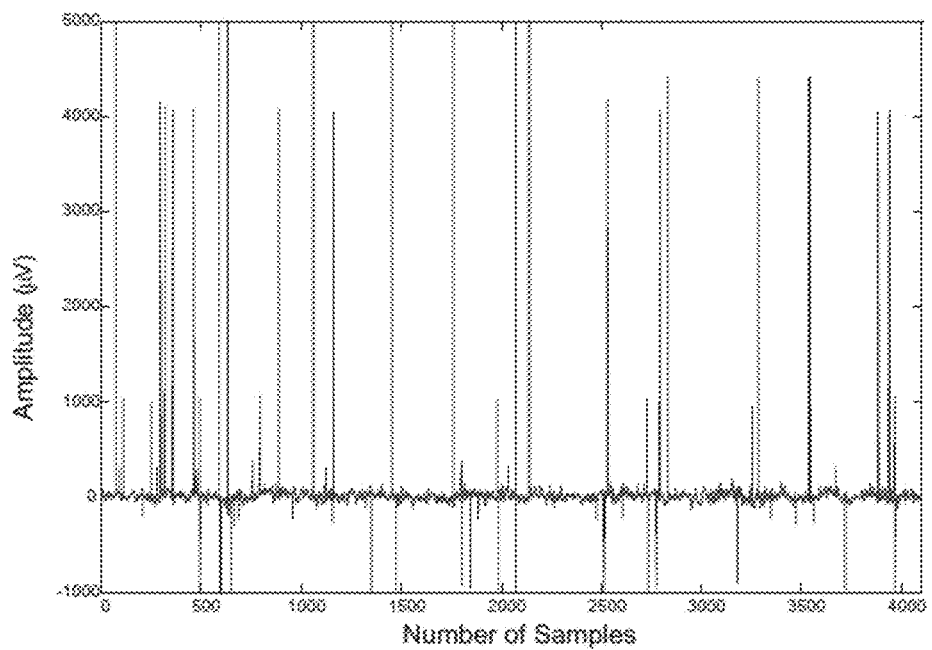
Figure 10:
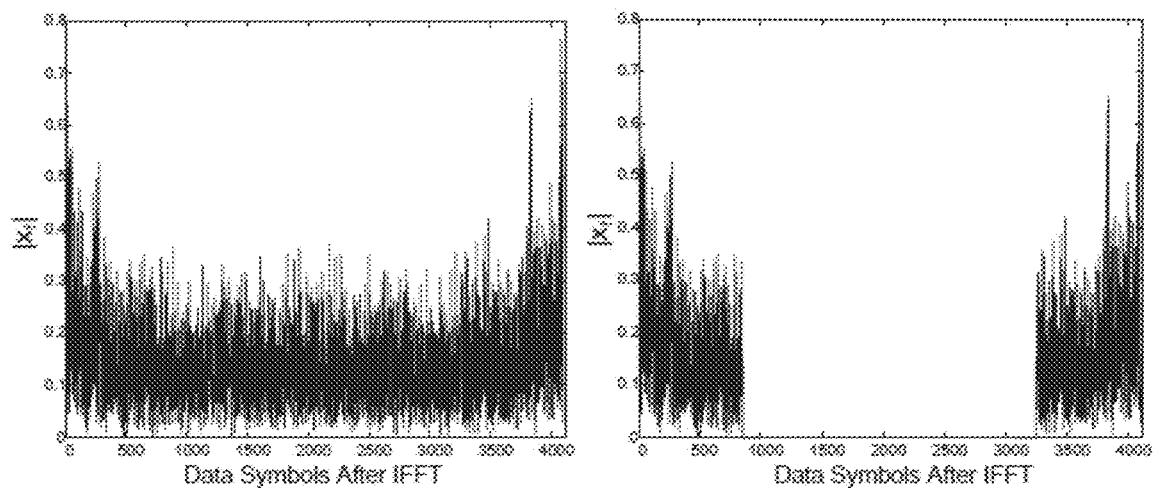
Figure 11:
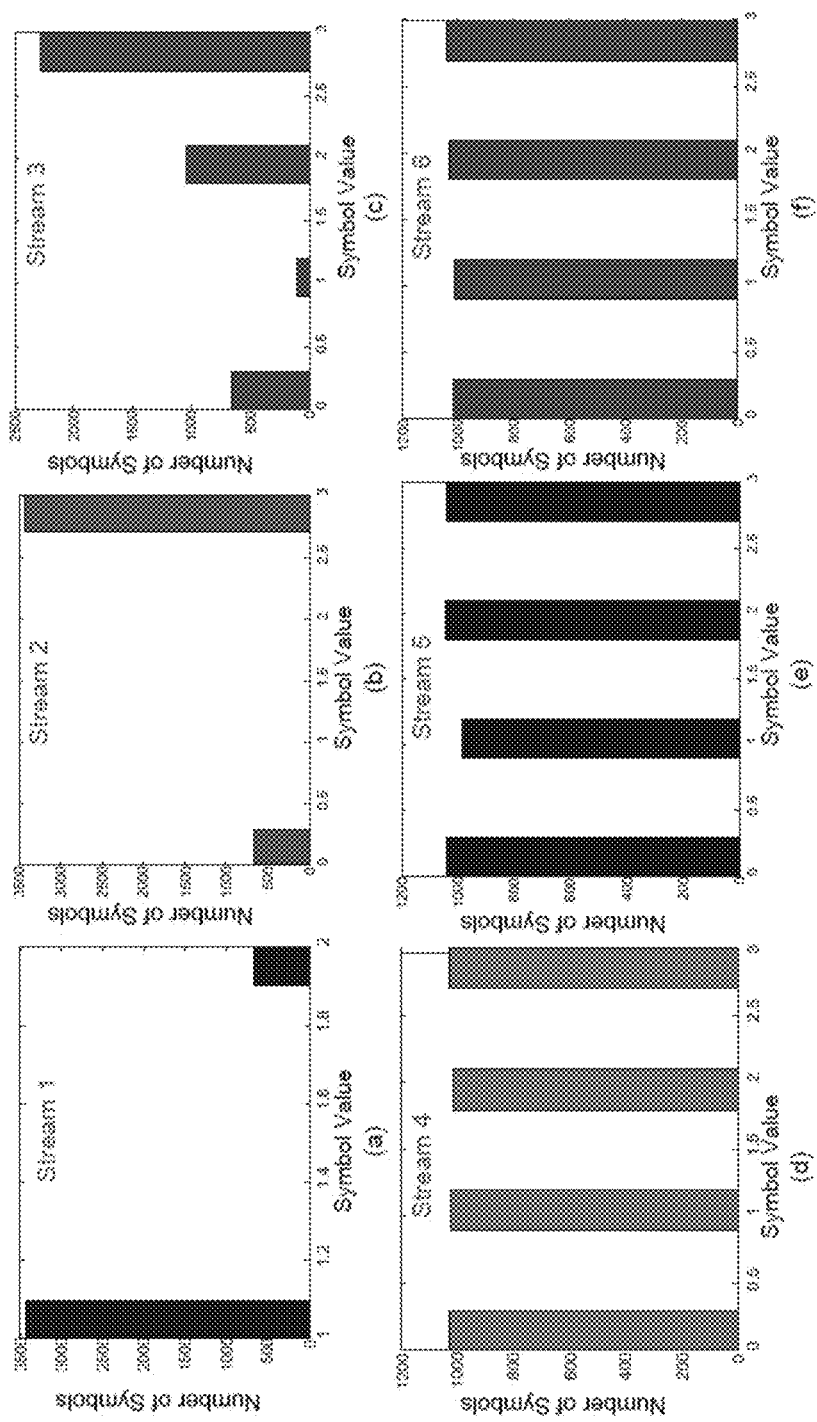
Figure 12:
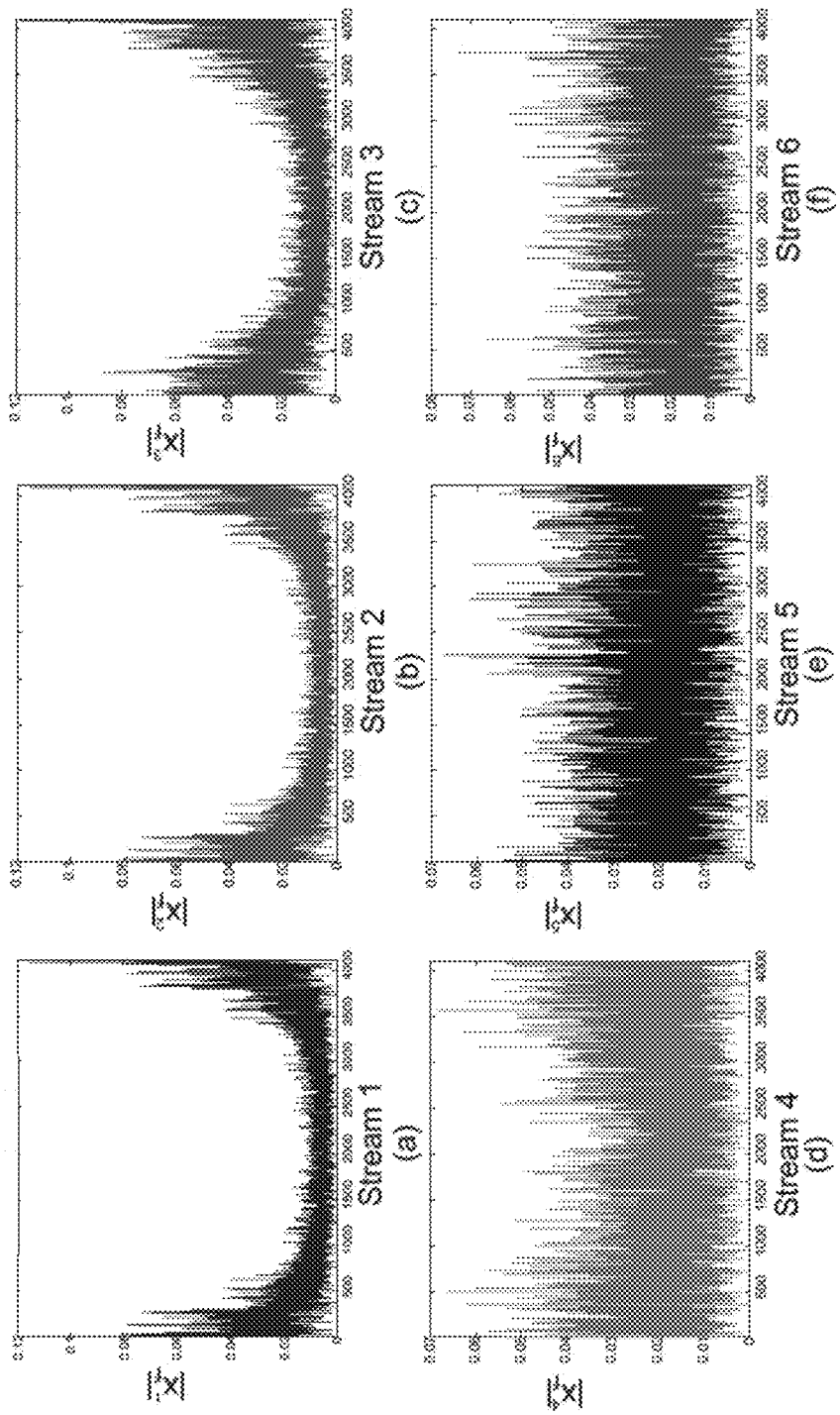
Figure 13:
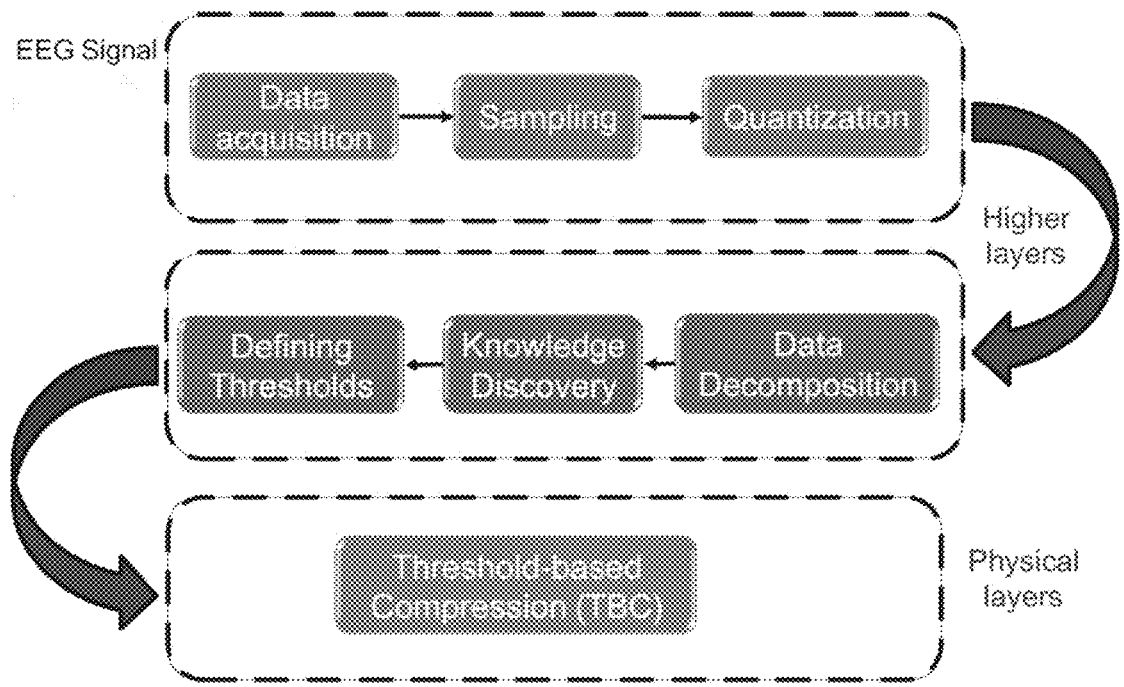
Figure 14:
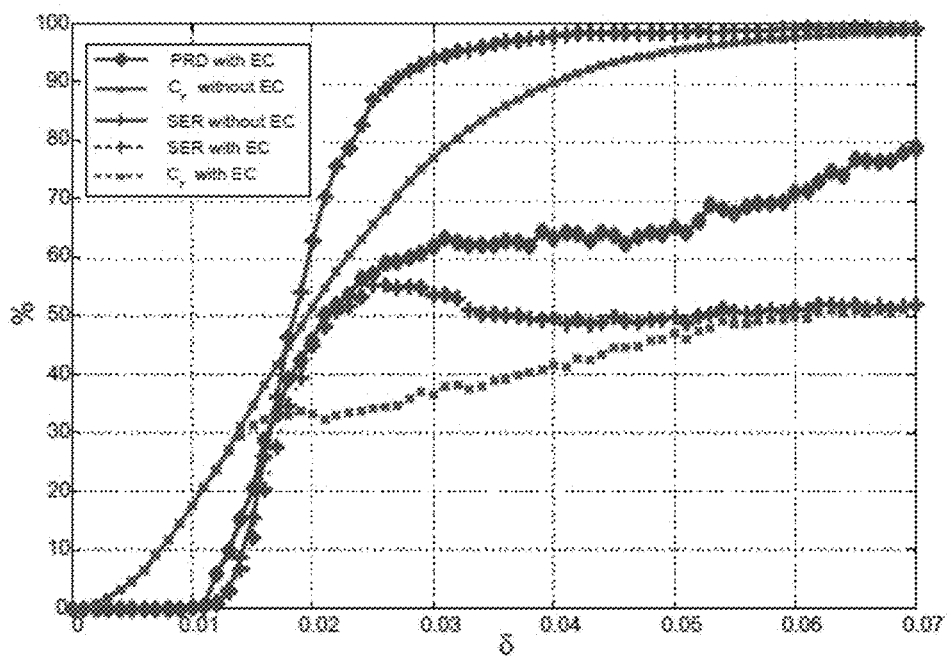
Figure 15:
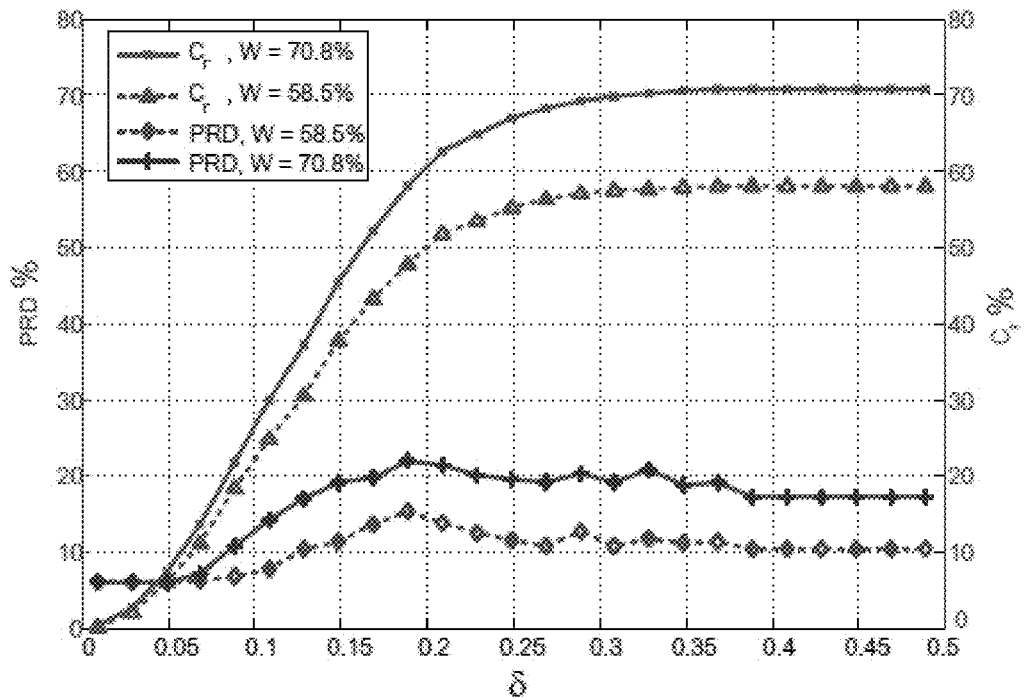
Figure 16:
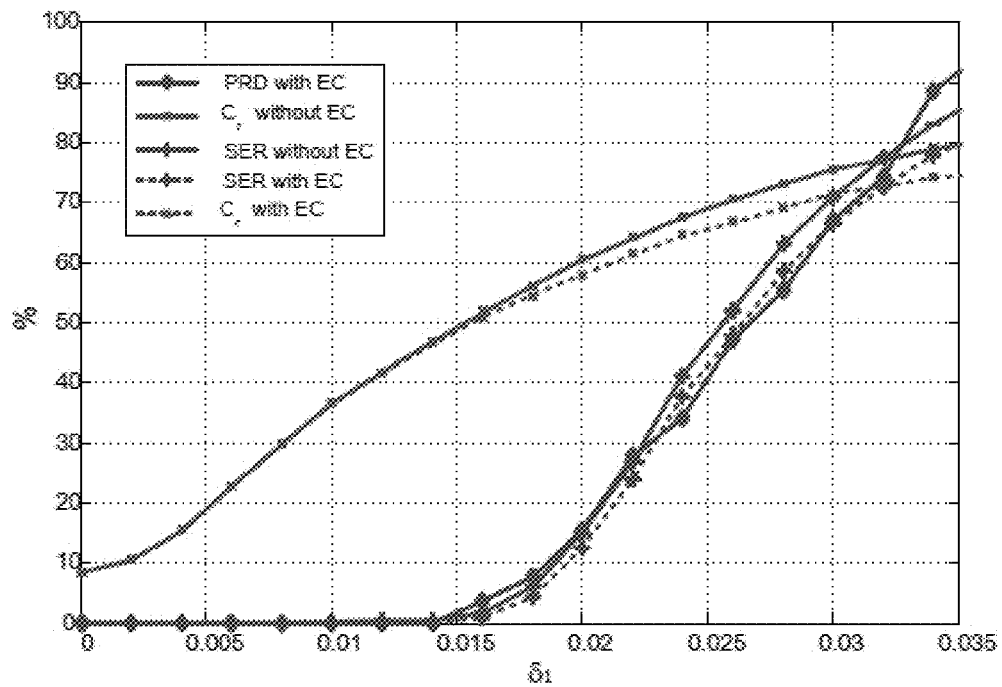
Figure 17:
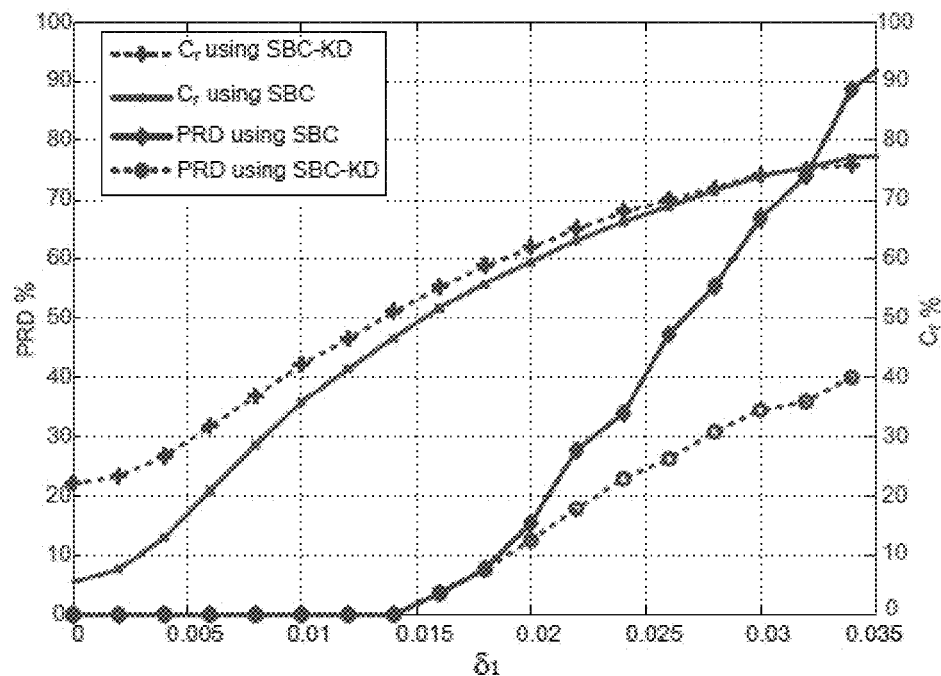
Figure 18:
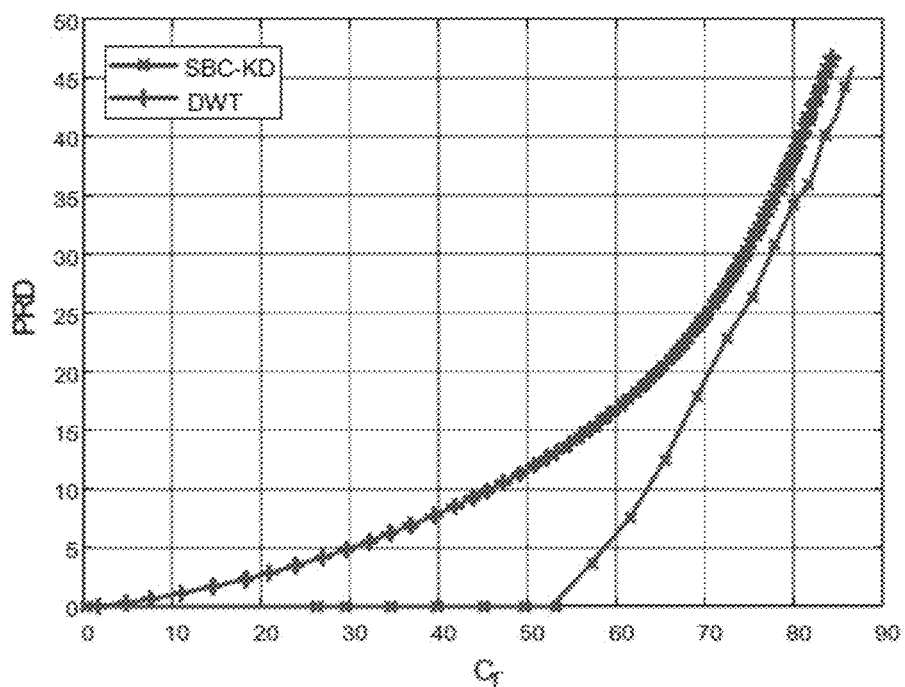
Figure 19:
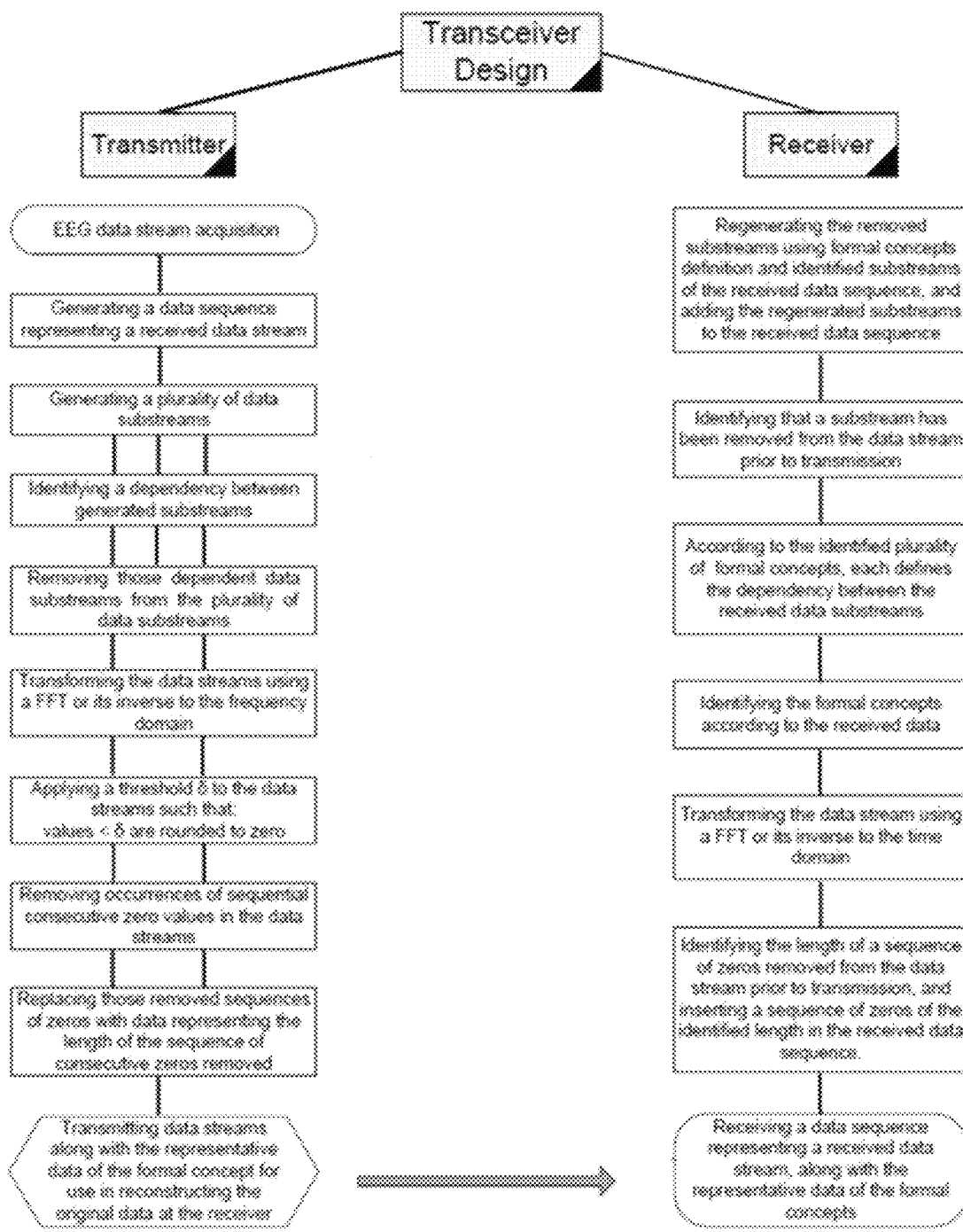

We now describe features of embodiments of the invention, by way of example only, with reference to the accompanying drawings of which FIG. 1 is a diagram illustrating the method of the present invention, embodied by a transmitter and a receiver according to the invention, FIG. 2 is a diagram of a transceiver architecture for IEEE802.11ah systems, FIG. 3 is a diagram of the transceiver architecture of the present invention for use with EEG, FIG. 4 is a table illustrating transformation of generated streams into a binary relation, FIGS. 5 and 6 are graphs illustrating an example EEG signal in the time domain, and in the frequency domain, respectively, FIG. 7 is a graph illustrating symbols after IFFT while considering 16-QAM modulation, FIGS. 8 and 9 are graphs illustrating the original EEG signal and reconstructed signal, respectively, FIG. 10 is a graph illustrating the generated symbols after IFFT while considering 256-QAM modulation, before compression (left) and after compression (right), FIGS. 11 and 12 are graphs illustrating generated symbols' streams before modulation and after IFFT, respectively, while considering QPSK modulation, FIG. 13 is a diagram showing the main steps of the SBC scheme of the present invention, FIG. 14 is a graph illustrating the effect of varying $C_r$ on signal distortion and SER when the TBC scheme and 16-QAM modulation are used, FIG. 15 is a graph showing the effects of varying the threshold $\delta$ on $C_r$ and signal distortion using TBC scheme and 256-QAM modulation, for different window size W, FIG. 16 is a graph showing the effect of varying threshold $\delta_1$ on the compression ratio, signal distortion, and sample error rate, when the QPSK modulation is used, FIG. 17 is a graph showing the effect of knowledge discovery on enhancing compression ratio and signal distortion for QPSK modulation, FIG. 18 is a graph showing the distortion variation for different values of compression ratio, for the proposed SBC-KD technique, and the DWT-level thresholding scheme, and FIG. 19 is a flow chart of methods according to example embodiments.

With reference to the drawings we describe the methods and devices involved.

The devices of the present invention are configured to operate broadly as outlined in FIG. 1 of the drawings, in line with the method described in detail below. The figure illustrates a system 10 incorporating a transmitter 12 and receiver 14. The figure illustrates the flow of data from EEG acquisition (performed using an EEG headset, for example, or by any other EEG acquisition device as is known in the art), via standard processing steps of sampling and quantization, to transmission. In this case, as shown in FIG. 1, the data is processed through a step of data decomposition, as described below, prior to transmission. The received signal is then reconstructed during a signal reconstruction step at the receiver 14 (or at a processing device receiving the signal from the receiver). The modules involved in this process are described below.

While the techniques described are suitable for EEG data, it should be appreciated that the techniques may be applied to other data sources and data types.

Sampling

Let the original continuous-time electroencephalography (EEG) waveform s(t) have a duration of T seconds. The waveform is sampled at a constant interval of $T_s$ seconds to yield Ns discrete-time consecutive samples. The sampling frequency is then given as $F_s = 1/T_s$ Hz.

Hence, $$s_n = s(t)\delta(t-nT_s) = s(nT_s) \quad (1)$$

for $n \in \{0, 1, \ldots, N_s-1\}$, where $\delta(\cdot)$ is the Dirac delta function. Our adopted notations are set out in Table II.

TABLE II

SUMMARY OF USED NOTATIONS.

| Notation | Definition |
| --- | --- |
| T | EEG waveform duration |
| $N_s$ | Number of samples |
| $F_s = N_s/T$ Hz | Sampling Frequency |
| $T_s$ | Inter-sample duration |
| L | Number of bits per sample |
| M | Number of symbols per sample |
| K = L/M | Number of bits per symbol |

Quantization: The continuous amplitude of each sampled signal is quantized using an L-bit analog-to-digital converter (ADC) to one of $2^L$ levels, yielding the quantized signal $\tilde{x}_n$ time index n. Each signal $\tilde{x}_n$ holds a signed integer value in range $\{-2^{L-1}, \ldots, 2^{L-1}-1\}$. We can express the quantized signal in vector form as $$\underset{N_s \times 1}{\tilde{x}} = [x_0 \, x_1 \, \ldots \, x_{N_s-1}]^T. \quad (2)$$

Data Decomposition: The collected EEG quantized samples are written as a sequence of symbols that depend on the adopted modulation. Such symbols are then divided into multiple streams, which are processed using Formal Concept Analysis in order to discover the correlation existing between the different streams. The streams that are found to be independent of each other, are compressed end transmitted, while others are discarded. Additionally, each steam is compressed separately, using a compression threshold that suits its characteristics, thus farther increasing the compression ratio.

Threshold-Based Transceiver: To comply with the current and future trends, we start from the typical OFDM transceiver architecture (depicted in FIG. 2-(*a*)), and add two simple blocks: the Threshold-based Compression (TBC) and the FFT Vector Reconstruction, Nevertheless, our solution can be applied to other transceiver architectures such as the one adopted by the IEEE802.11ah and the IEEE802.15.4g standards.

In the proposed transceiver architecture, it is assumed that the available quantized samples are encoded into an unsigned binary sequence via the L-bit ADC. We first turn the generated signed-inner samples into non-negative integers by a simple shift, i.e., $$x_n = \tilde{x}_n + 2^{L-1}. \quad (3)$$

Then the symbols are forwarded to the modulation and IFFT modules. Details on am TBC and FFT vector reconstruction blocks are discussed in the following section.

FIG. 2 provides a block diagram of the transceiver architecture for IEEE802.11ah systems, and FIG. 3 shows the adopted EEG transceiver of the invention. It should be noted in those Figures that both the transmitter 12 and receiver 14 include a step involving insertion (and removal, respectively) of guard intervals, as is known in the art (a guard interval being a time gap inserted to avoid interference between distinct transmissions).

The physical layer's characteristics are leveraged to decompose quantized EEG samples into multiple streams of symbols, such that the dependency between different streams is reduced, and hence, compressibility is improved. In general terms, the signal is split (i.e. decomposed) into multiple streams. The streams are then analysed to discover dependencies and similarities between the stream content, and this information is then used to limit or reduce the data for transmission. In more detail, the steps involved are as follows.

In broad terms, the method involves generating a data sequence representing a received data stream. In other words, a stream of symbols is generated as a representation of the data stream that is received from a measuring device such as an EEG headset, for example, or from another data source. The method then involves generating a plurality of data substreams, each comprising a portion of the data sequence. These substreams can then be analysed to determine whether any formal concept exists, linking one or more of the substreams. One or more formal concepts are identified, each defining a dependency between a first one of the data substreams and one or more further ones of the data substreams that are dependent on the first data substream. To compress the data for transmission, the redundant dependent substreams can be removed, since they can be recreated at the receiver based on knowledge of the formal concept, and the substream to which they are linked by the formal concept.

To this end, once an applicable formal concept has been identified, the transmitter may include data representative of that formal concept. This may involve either describing the formal concept, or otherwise allowing the receiver to identify it (for example, by reference to a stored record of formal concepts).

At the receiver side, the receiver identifies that a substream has been removed from the data stream prior to transmission. This may occur based on identification of a symbol or token identifying the removal of a substream at a point in the data, or may identify a formal concept directly and/or provide a definition of that formal concept. This enables the receiver to identify a specific formal concept and a substream of the data to which the formal concept should be applied to recreate the removed substream. In response to identifying this information, the receiver may regenerate a data substream using the formal concept definition and the identified substream of the received data sequence, and add the regenerated data substream to the received data sequence.

A. Data Decomposition

We first decompose the EEG signal $x_n$ into multiple streams of symbols $x^m$, for $m \in \{1, 2, \ldots, M\}$. Let the binary encoded sequence of $x_n$ be denoted as $b \in \mathbb{F}_{2^L}$, with $\mathbb{F}_p$ being the Galois Field of order p. Hence, b is a sequence of L bits on the form $$b = [\underbrace{b_{K-1}^{(M-1)} \ldots b_0^{(M-1)}}_{b^{(M-1)}} \ldots \underbrace{b_{K-1}^{(0)} \ldots b_0^{(0)}}_{b^{(0)}}]^{L \text{ bits}} \quad (4)$$

where $b^{(m)}$ is the group of K bits composing the m-th symbol, with $m \in \{1, \ldots, M\}$, where K and M depend on the modulation type. More specifically, M is the number of symbols per sample, which depends, not only on the modulation order O, but also on the number of bits per sample L, as follows:

$$M = \frac{L}{\log_2(O)} = \frac{L}{K}. \quad (5)$$

Then, $x_n$ can be rewritten as:

$$x_n = \sum_{m=0}^{M-1} \sum_{k=0}^{K-1} 2^{mK+k} b_k^{(m)} = \sum_{m=0}^{M-1} 2^{mK} x^m, \quad (6)$$

with $$x^m = \sum_{k=0}^{K-1} 2^k b_k^{(m)}. \quad (7)$$

In conclusion, the bit stream block $b^{(m)}$ is simply the binary representation of $x^m$, which implies $x^m \in \{0, 1, \ldots, 2^K-1\}$.

B. Knowledge Discovery

We leverage the symbol streams that are created, and the compression ratio can be further increased by discovering the correlation between different streams. In summary, using Formal Concept Analysis (FCA) for knowledge discovery, we select the minimal-representative streams so as to minimise the number of transmitted data streams without losing knowledge.

We start by introducing the basic notions used to induce a binary relation between the generated streams. Let $\mathcal{O}$ be the set of streams (i.e., objects), $\mathcal{A}$ the set of symbols' values (i.e., attributes), and I the binary relation on the universe $\mathcal{U} = \mathcal{O} \times A$ that defines which objects have which attributes. In order to transform our streams into formal context of $(\mathcal{O}, A, I)$, we consider the attributes $\alpha_v$ of each symbol s to be all the possible values it may take, depending on the employed modulation, for $v \in \{0, 1, \ldots, 2^K-1\}$, and $\alpha_v \in \{0, 1\}$. Thus, the vector of attributes A for each stream $x^m$ is defined as $$A(\tilde{x}^n) = \begin{bmatrix} a_0 \ldots a_{2^K-1} & \ldots & a_0 \ldots a_{2^K-1} \\ s_1 & & s_{N_s} \end{bmatrix}, \quad (8)$$

where A represents the possible values of each symbol.

The aim is to obtain the dependency between different streams through finding the minimal set of formal concepts covering our relation. (O,A) is a formal concept if A is the set of all attributes shared by the objects O, and in the same time O is the set of all objects that have all attributes in A.

We refer to the implications as the minimal set of rules, by which we can infer some attributes from others. We can derive formal concepts from our formal context using the derivation operators or difunctional decomposition. Difunctional decomposition enables obtaining the isolated points of a binary relation through calculating the Fringe Relation. This fringe relation is, by definition, a difunctional relation, and all its elements are isolated points. Thus, the formal concepts can be easily obtained by finding such isolated points, since if (a; b) is an isolated point, by definition it is included in one concept only.

Once the formal concepts are derived, implications can be identified, hence transmitting only the minimal-representative number of streams. For the sake of clarity, we describe the adopted procedure by referring to a toy example where a data length of 20 samples with QPSK modulation is considered.

Step 1: Generation of Formal Context.

Consider the generated streams of symbols. We consider each stream as an object with attributes corresponding to its symbols' values. As an example, FIG. 4 illustrates the formal context of 6 streams with 20 symbols.

Step 2: Identifying Formal Concepts.

The generated binary relation are then decomposed into a set of concepts, using the algorithm presented by R. Khcherif, M. M. Gammoudi, and A. Jaoua, "*Using difunctional relations in information organization*," Information Sciences 125, pp. 153-166, 2000, for example. However, in order to identify the dependency between different streams, we leverage a concept referred to as "shadow concept": considering not only the attributes for which the relation I is equal to 1, but also the negation of the attributes, i.e., the attributes values for which the relation is equal to 0. In this case, both the attributes and the negation of the attributes form the identified concept.

Step 3: From Concepts to Implications.

Based on the identified concepts, we derive the implications that can be used to effectively eliminate the streams that can be retrieved at the receiver using their implications with other received streams. For instance, looking at FIG. 4, we can easily identify from the obtained concept that $O_2 \rightarrow O_1$, where $\rightarrow$ stands for the implications, since $O_2 = |O_1 + 2|_4$ for $O_2$, $O_1 \in [0, \ldots, 3]$.

Step 4: Elimination.

For each obtained concept, we transmit only one stream and eliminate other streams that belong to the same concept. Then, the retrieval process is carried out at the receiver using the identified implications.

A. EEG Signal Characteristics

We first visualize and analyze the EEG signal in the time and frequency domains in order to understand its properties and obtain the best approach of processing and transmission. A normal continuous EEG signal in the time domain is shown in FIG. 5. Using frequency domain analysis, we can significantly reduce the amount of data to be transmitted. This can be done through transforming the collected EEG data into the frequency domain using FFT, which is a classic frequency analysis method with complexity O(N log N).

Looking at the generated spectrum shown in FIG. 6, we observe that it is to some extent sparse, or compressible. Here "compressible" means that the generated spectrum f has a large number of frequencies whose entries (i.e., Fourier coefficients) have magnitudes that are small compared to the norm off (i.e., the energy of f). Thus, we can efficiently reduce transmission energy consumption for such Fourier sparse signals through transmitting only energetic Fourier coefficients, while retrieving original signal at the receiver side.

B. Threshold-Based Compression

Motivated by the EEG signal characteristics in the frequency domain, we update the OFDM transceiver architecture at the physical layer to support our compression scheme. Unlike the prior art compression techniques that are applied at the higher layers, we convey our compression scheme into the physical layer exploiting the existing OFDM transceiver's components in order to perform efficient compression without adding much complexity.

As mentioned, given the basic OFDM transceiver architecture in FIG. 2, we have added two blocks in order to implement our TBC scheme, namely, the TBC and the FFT Vector Reconstruction, as set out in FIG. 3. In the TBC block, leveraging the fact that several Fourier coefficients $x_f$ of the EEG signal x have negligible magnitude (see FIG. 7), we consider as 0s all symbols with magnitude lower than a predefined threshold $\delta$ (see FIG. 10). The threshold is set according to the channel characteristics and the maximum distortion that can be tolerated at the receiver side. Clearly, the higher the value of $\delta$, the larger the compression ratio and the resulting distortion. Then, whenever we have a number of consecutive zeros greater than two, the transmitter does not send them, but it notifies the receiver about the length of this sequence and its position in the stream of transferred data. We note that efficient techniques like run-length encoding can be leveraged to perform such tasks.

So, in general terms, the compression method involves transforming the data stream using a Fast Fourier Transform or its inverse to convert the data stream from the time domain to the frequency domain. In the frequency domain, as discussed above, a large part of the data stream is likely to consist of low values—approaching zero. Therefore, it is possible to apply a threshold $\delta$ to the data stream such that values less than $\delta$ are rounded to zero, without losing a significant portion of the data content.

Subsequently, the stream may be further compressed by removing occurrences of sequential consecutive zero values in the data stream and replacing those removed sequences of zeros with data representing the length of the sequence of consecutive zeros removed.

At the receiver side, the FFT vector reconstruction block is responsible for adding zeros in the received vector at the positions of the ignored symbols before forwarding it to the FFT block. The latter will then demodulate the received symbols and reconstruct the EEG signal.

C. Error Correction

In order to quantify the achieved compression gain compared to the consequent signal distortion due to our compression scheme, we define the compression ratio as $$C_r = \left(1 - \frac{\gamma}{\mu}\right) \times 100 \tag{9}$$

where $\gamma$ is the number of data symbols to be transmitted, and $\mu$ is the number of the generated data symbols after modulation. While the signal distortion is quantified using Percent Root man square Difference (PRD), which is given by $$PRD = \sqrt{\frac{\sum_{i=1}^{N}[x(i) - x_r(i)]^2}{\sum_{i=1}^{N}[x(i) - \bar{x}]^2}} \times 100, \tag{10}$$

where $\tilde{x}$ is the average value of the original quantized signal, and $x_r$ is the reconstructed one.

Interestingly, using our EEG compression transceiver we can easily define some of the wrong reconstructed samples at the receiver side. As shown in FIGS. 8 and 9, some of the wrong samples have very large amplitude compared to the correct samples. This advantage can be used as an Error Correction (EC) scheme in order to decrease Sample Error Rate (SER) and signal distortion at the receiver through: (i) identifying received samples with relatively large amplitude (samples with error), (ii) retransmitting the reconstructed samples with error.

Despite the achieved compression ratio using TBC, it has been found that it is of prominent importance to further analyse the effect of symbol mapping and modulation on EEG signal characteristics in order to enhance the compression ratio. As noted from FIG. 6 and FIG. 7, the EEG signal characteristics after modulation and IFFT modules have been changed and turned to be less compressible.

This is mainly due to the effect of symbol mapping and modulation, since representing each data sample with multiple symbols turns the generated symbols after IFFT to be less compressible, i.e., most of the generated symbols after IFFT will have large magnitudes and therefore cannot be neglected.

D. Higher-Order Modulation

To tackle the problem of symbol mapping effect on EEG sparsity and increase compression efficiency of our transceiver, we study the characteristics of generated symbols after Fourier transform with and without symbol mapping and modulation (see FIG. 6 and FIG. 7). Exploiting higher-order modulation can help in increasing compression ratio of the transceiver through representing each EEG sample in one symbol, which relieves the effect of symbols mapping.

However, as shown in FIG. 10 (left-hand graph), magnitudes of the generated symbols after IFFT $|x_f|$ are still less compressible compared to the original case without modulation, i.e., in FIG. 6 (even after considering the higher-order modulation). As a result, when applying our threshold-based compression, some of the important symbols may be also neglected. To avoid this, we apply Symbols Masking before compression.

This masking is based on our prior knowledge about the EEG characteristics in the frequency domain. We define a window size W which is the percentage of compressible symbols relative to the total number of symbols. Using this masking, we define the less important symbols of $x_f$ to be passed by the TBC scheme, while isolating more important symbols from compression (see FIG. 10, right-hand graph). Using such masking with higher-order modulation can significantly mitigate the effect of symbols mapping and modulation on EEG characteristics. By doing so, we could obtain higher compression ratio compared to initial TBC scheme with lower order modulation, as will be shown in simulation results.

For the hardware implementation complexity, we remark that the proposed threshold-based compression results in adding few numbers of real valued operations compared to multicarrier modulations techniques considered for 5G (e.g., filtered orthogonal frequency division multiplexing (fOFDM), filter bank multicarrier (FBMC), and cyclic convolution based FBMC). These adopted modulations techniques result in increasing the computational complexity compared to conventional OFDM.

E. Stream-Based Compression

Due to the quality of wireless channel, hardware design, or standards limitations, leveraging higher-order modulation may not be recommended in all cases. Thus, in order to make our transceiver adaptive for different channel conditions and modulation schemes, we propose a Stream-Based Compression (SBC) scheme. Leveraging the generated symbol streams in Section IV, the compression ratio can be further increased as follows. The independent streams of symbols are forwarded to the modulation and IFFT blocks, thus at TBC block, we can deal with each stream separately using different values of the δ threshold. This, as also shown in the simulation results section, yields a greater overall compression ratio.

For instance, using QPSK modulation and L=12 bits, we will generate 6 streams of symbols. The symbols in each stream will have different values before modulation (see FIG. 11) and after IFFT (see FIG. 12). Thus, we can set per-stream thresholds so that each stream will be compressed as much as possible while still meeting the requirement on the maximum allowed distortion.

We note that discovering the dependency between different streams and selecting only the independent streams is performed before IFFT (i.e., it pertains to the higher layers of the transceiver architecture, while only the threshold-based compression is done after IFFT, i.e., in the physical layers of the transceiver. Thus, to summarize, the main steps of the SBC scheme are as follows (see FIG. 13):

Higher-layers steps, which include stream creation, knowledge discovery, and defining the threshold δ, for individual streams.

Physical-layer step, which includes TBC.

While at the receiver side, the inverse process is adopted through: (i) using FFT vector reconstruction, which is responsible for adding zeros in the received vector at the positions of the compressed symbols before forwarding it to the FFT, and (ii) leveraging obtained dependency between different streams to retrieve discarded streams from transmission.

Simulation Results

In order to derive simulation results, the system model shown in FIG. 1 was implemented for use with the EEG dataset as used in R. Andrzejak, K. Lehnertz, C. Rieke, F. Mormann, P. David, and C. Elger, "*Indications of nonlinear deterministic and finite dimensional structures in time series of brain electrical activity: Dependence on recording region and brain state*," Physical Review E, 64, 061907, 2001. To quantify the performance gain provided by the present invention, both the compression ratio and the consequent signal distortion were investigated, while considering high signal-to-noise ratio (SNR) for the wireless channel. The simulation parameters used are set out in Table III.

TABLE III

SIMULATION PARAMETERS

| Parameter | T | $N_s$ | $T_s$ | L | M |
|---|---|---|---|---|---|
| Value | 23.6 sec | 4096 | 0.0058 | 12 bits | $\in \{2, 3, 4, 6\}$ |

First, the performance of the proposed TBC transceiver, described above, was assessed without performing the signal decomposition into different symbol streams. FIG. 14 shows the performance gain of the transceiver when the 16-QAM modulation (i.e., M=3 symbols per sample) is used. Herein, we gradually increase the compression ratio $C_r$ by increasing the threshold δ furthermore, both the cases with and without our Error Correction (EC) scheme are considered. As expected, with increasing δ, the Sample Error Rate (SER) and signal distortion (PRD) increase as well (see FIG. 14).

However, when EC is applied, SER and PRD reduce significantly thanks to the retransmission of the erroneous samples. On the contrary, the actual or effective Cr decreases due to the higher retransmission overhead. Importantly, these results show that, using the well-known OFDM transceiver architecture with slight modifications, we can obtain about 25% compression ratio while keeping SER and distortion below 10%, which is acceptable by many applications.

FIG. 15 highlights the increase in $C_r$ that we can obtain by leveraging higher-order modulation and symbols masking. We can achieve about 60% $C_r$ while keeping distortion around 10%. Also, with larger window size W, the compression ratio grows at the expense of an increased signal distortion. We note that, depending on the quality of the wireless channel, the modulation order can be increased (i.e., enabling high-order modulations for low channel errors), hence the compression ratio, while still meeting the application requirements.

Next, we assess the performance of the proposed SBC scheme in Section IV, i.e., we also account for the benefits brought by the decomposition of the signal into streams of symbols and their processing. Interestingly, our SBC transceiver can support both lossless and lossy compression. As depicted in FIG. 16, we can achieve about 45% compression ratio at 0% SER and distortion, or about 55% compression ratio at less than 10% SER and distortion. Herein, we used the QPSK modulation with two compression thresholds $\delta_1$ and $\delta_2$, where $\delta_2$ is fixed to 0.011 while $\delta_1$ varies. In particular, $\delta_2$ was used for stream 3, since its values have high variability before modulation and low amplitude after IFFT (see FIG. 11 and FIG. 12), while 61 was adopted for the other streams. Interestingly, such results show that, thanks to the signal decomposition into streams, we can significantly increase the compression ratio while applying low-order modulation schemes.

The transceiver performance further improves if the SBC-KD scheme is used. Indeed, by applying knowledge discovery and transmitting only the minimal-representation streams, we can considerably reduce the amount of transferred data while still accurately reconstructing the signal at the receiver side. The results in FIG. 17 demonstrate that in this case we can obtain, roughly, 50% compression ratio at 0% SER and distortion, or 67% compression ratio with less than 20% distortion.

Finally, in FIG. 18 we compare the performance of the proposed SBC-KD scheme with the DWT technique. Wavelet-based compression techniques consist of transmitting the most significant wavelet coefficients. Comparing to DWT-Level thresholding, we obtain 13% reduction in the PRD for compression ratios up to 50%, while achieving 5% reduction in the PRD for higher values, namely, up to 80%, of the compression ratio. Furthermore, we can use the proposed scheme for lossless compression for compression ratios up to 50%, which shows significant gains over DWT in applications requiring zero distortion and high quality analysis of the vital signs.

This achieved increase in compression ratio also reflects on the transmission energy consumption (see Table IV, below). Thus, a significant amount of energy consumption can be saved using the proposed compression scheme. Also, as energy consumption decreases with increasing compression ratio and distortion, our scheme can be adapted to maintain the best tradeoff between energy consumption and signal distortion, based on application requirements and energy availability.

TABLE IV

TRANSMISSION ENERGY CONSUMPTION VS. COMPRESSION RATIO

| Transmission Energy (mJ) | $C_r$, % |
|---|---|
| 163.84 | 0 |
| 147.46 | 10 |
| 114.69 | 30 |
| 65.54 | 60 |
| 49.15 | 70 |
| 24.58 | 85 |

In general terms, the transmitter 10 of the present invention includes a sensing or acquisition device—either a device suitable to detect and record a signal, for example, or an input for receiving a detected or recorded signal. In embodiments this is an EEG acquisition device or an input for receiving an encoded EEG signal.

The transmitter 12 includes a processor and/or other hardware (such as memory and storage hardware) suitable for performing sampling of the data signal and a quantization step, in which the signal is converted to a stream of data with discrete values/magnitudes.

As shown in FIG. 3, the transmitter 12 of embodiments is operable to perform IFFT to convert the frequency domain signal to a time domain signal. In embodiments, the transmitter 12 carries out threshold-based compression to remove sequences of 0s (or low values that have been converted, using a threshold, to 0 value) from the signal.

The transmitter 12 than carries out data decomposition and thresholding steps, as described above, before transmission. Of course the transmitter includes suitable equipment for transmitting a radio frequency signal (or other wireless signal) such as those known generally in the art.

As shown in FIG. 13 of the attached drawings, a first layer involves data acquisition, sampling and quantization of the signal as is generally known in the art. A second layer of further computation according to embodiments of the invention involves data decomposition, knowledge discovery and defining suitable thresholds for processing the data, as described above. A physical layer (i.e. a circuit-based component of the transmitter) provides threshold-based compression prior to transmission of the signal.

The receiver 14 includes a suitable wireless signal receiving device preferably a threshold-based receiver as described. The receiver 14 according to embodiments of the invention, and as shown in FIG. 3, provides circuitry, and/or a processor and/or memory and other storage devices, operable to remove guard intervals that were inserted prior to transmission. The receiver 14 is further configured to perform FFT vector reconstruction in the case where strings of 0s have been removed prior to transmission to expand the signal to include those 0s, prior to FFT, to convert from the time domain back to the frequency domain.

Finally, symbol demapping/demodulation takes place prior to outputting the received and processed data (encoded EEG data, for example).

Representative features are set out in the following clauses, which stand alone or may be combined, in any combination, with one or more features disclosed in the text and/or drawings of the specification.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realising the invention in diverse forms thereof.

Although certain example embodiments of the invention have been described, the scope of the appended claims is not intended to be limited solely to these embodiments. The claims are to be construed literally, purposively, and/or to encompass equivalents.

The invention claimed is:

1. A method of compressing a data stream for transmission, including:

generating a data sequence representing a received data stream, generating a plurality of data substreams, each comprising a portion of the data sequence, including quantizing the data sequence, writing the data sequence as a sequence of symbols that depend on an adopted modulation, and dividing the data sequences into data substreams, identifying a formal concept defining a dependency between a first one of the data substreams and one or more further ones of the data substreams that are dependent on the first data substream, removing those dependent data substreams from the plurality of data substreams, transmitting the remaining data substreams.

2. A method according to claim 1, wherein the step of identifying a formal concept includes identifying a plurality of formal concepts, each defining a dependency between a first one of the data substreams and one or more of the further ones of the data substreams that are dependent on the first data substream.

3. A method according to claim 1, further including the step of transmitting data representative of the formal concept for use in reconstructing the removed data substreams at the receiver.

4. A method according to claim 1 further including transforming the data stream using a Fast Fourier Transform or its inverse to convert the data stream from the time domain to the frequency domain.

5. A method according to claim 4 further including applying a threshold $\delta$ to the data stream such that values less than $\delta$ are rounded to zero.

6. A method according to claim 5 further including a step of further compressing the data stream by
removing occurrences of sequential consecutive zero values in the data stream and
replacing those removed sequences of zeros with data representing the length of the sequence of consecutive zeros removed.

7. A system including a transmitter and a processor, wherein the processor is configured to:
generate a data sequence representing a received data stream,
generate a plurality of data substreams, each comprising a portion of the data sequence, including quantizing the data sequence, writing the data sequence as a sequence of symbols that depend on an adopted modulation, and dividing the data sequences into data substreams,
identify a formal concept defining a dependency between a first one of the data substreams and one or more further ones of the data substreams that are dependent on the first data substream, and
remove those dependent data substreams from the plurality of data substreams, wherein the transmitter is configured to transmit the remaining data substreams.

8. A system according to claim 7, wherein the transmitter and processor is further configured as an Orthogonal Frequency Division Multiplexing Transceiver, the Orthogonal Frequency Division Multiplexing Transceiver including a Threshold-based Compression module that operates on the plurality of substreams.

9. A method of compressing a data stream for transmission, including:
generating a data sequence representing a received data stream,
generating a plurality of data substreams, each comprising a portion of the data sequence,
identifying a formal concept defining a dependency between a first one of the data substreams and one or more further ones of the data substreams that are dependent on the first data substream, including identifying an existing correlation between the first one of the data substreams and one or more further ones of the data substreams, the existing correlation considering both the attributes and the negation of the attributes of the data substreams,
removing those dependent data substreams from the plurality of data substreams, and
transmitting the remaining data substreams.

10. A method according to claim 9, wherein the step of identifying a formal concept includes identifying a plurality of formal concepts, each defining a dependency between a first one of the data substreams and one or more of the further ones of the data substreams that are dependent on the first data substream.

11. A method according to claim 9, further including the step of transmitting data representative of the formal concept for use in reconstructing the removed data substreams at the receiver.

12. A method according to claim 9, further including transforming the data stream using a Fast Fourier Transform or its inverse to convert the data stream from the time domain to the frequency domain.

13. A method according to claim 9, further including applying a threshold $\delta$ to the data stream such that values less than $\delta$ are rounded to zero.

14. A method according to claim 13 further including a step of further compressing the data stream by removing occurrences of sequential consecutive zero values in the data stream and replacing those removed sequences of zeros with data representing the length of the sequence of consecutive zeros removed.

15. A system including a transmitter and a processor, wherein the processor is configured to:
generate a data sequence representing a received data stream,
generate a plurality of data substreams, each comprising a portion of the data sequence,
identify a formal concept defining a dependency between a first one of the data substreams and one or more further ones of the data substreams that are dependent on the first data substream, including identifying an existing correlation between the first one of the data substreams and one or more further ones of the data substreams, the existing correlation considering both the attributes and the negation of the attributes of the data substreams, and
remove those dependent data substreams from the plurality of data substreams, wherein the transmitter is configured to transmit the remaining data substreams.

16. A system according to claim 15, wherein the transmitter and processor is further configured as an Orthogonal Frequency Division Multiplexing Transceiver, the Orthogonal Frequency Division Multiplexing Transceiver including a Threshold-based Compression module that operates on the plurality of substreams.

* * * * *